(12) United States Patent
Potter et al.

(10) Patent No.: US 6,465,522 B1
(45) Date of Patent: Oct. 15, 2002

(54) ANTHRAQUINONE ANTICANCER DRUGS

(75) Inventors: Gerard Andrew Potter, Leicester; Laurence Hylton Patterson, Great Glen, both of (GB); Paul Teesdale-Spittle, Wellington (NZ); Zennia Paniwynk, Oldham (GB)

(73) Assignee: De Montford University (GB)

( * ) Notice: Subject to any disclaimer, the term of this patent is extended or adjusted under 35 U.S.C. 154(b) by 0 days.

(21) Appl. No.: 09/868,956

(22) PCT Filed: Dec. 9, 1999

(86) PCT No.: PCT/GB99/04158

§ 371 (c)(1),
(2), (4) Date: Nov. 7, 2001

(87) PCT Pub. No.: WO00/38734

PCT Pub. Date: Jul. 6, 2000

(30) Foreign Application Priority Data

Dec. 24, 1998 (GB) .............................. 9828670

(51) Int. Cl.$^7$ .......................... A61K 31/135; C09B 1/16
(52) U.S. Cl. ........................ 514/646; 514/649; 552/243
(58) Field of Search ......................... 552/243; 514/646, 514/649

(56) References Cited

FOREIGN PATENT DOCUMENTS

WO    WO99/40944    8/1999

Primary Examiner—Alton N Pryor
(74) Attorney, Agent, or Firm—Wallenstein & Wagner, Ltd.

(57) ABSTRACT

A molecule of formula (I);

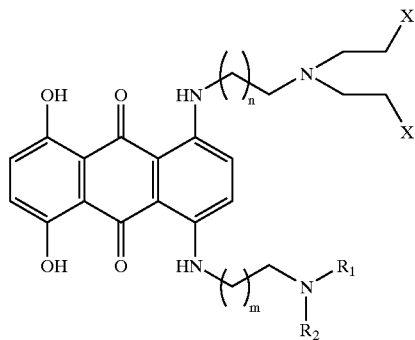

wherein:

X is a halogen, or a substituted sulfonate group;

m=1–5;

n=1–5;

$R_1$, $R_2$=H, C1–4 lower alkyl or C1–4 lower alkyl chain having additional functionality; and the amino group $-NR_1R_2$ linked to the anthraquinone is primary, secondary or tertiary or is a tertiary group in the N-oxide form having the formula $-N(O)R_1R_2$.

15 Claims, 1 Drawing Sheet

ANTHRAQUINONE ANTICANCER DRUGS

This application is a 371 of PCT/GB99/104158 files Feb. 9, 1999

The present invention concerns a novel family of anticancer drugs comprising an anthraquinone group linked to an alkylating agent, the agents having potent anticancer activity and displaying potent activity against drug-resistant tumours.

A wide range of chemicals is now available to treat cancers. However, the clinical response to anticancer agents in cancer chemotherapy is ultimately limited by the emergence of drug resistant tumours. For example the utility of the commonly used anticancer drug adriamycin (doxorubicin) is limited by the emergence of adriamycin-resistant tumours. Similarly, the utility of cisplatin, another commonly used anticancer agent, is limited in cancer chemotherapy by the emergence of cisplatin-resistant tumours. Therefore there is a need for new anticancer agents which are active against drug resistant tumours.

The present invention provides novel anticancer drugs that surprisingly display potent activity against tumours, particularly drug resistant tumours. According to the present invention there is provided a molecule comprising an anthraquinone linked to an alkylating agent and having the formula (I):

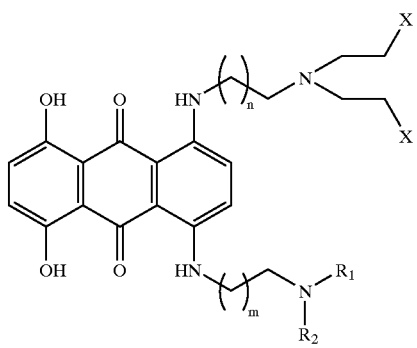

wherein:
X is a halogen, or a substituted sulfonate group;
in the linker group from the anthraquinone to the amino group, m=1–5;
in the linker group from the anthraquinone to the alkylating agent, n=1–5; and
the amino group —$NR_1R_2$ linked to the anthraquinone is primary, secondary or tertiary or is a tertiary group in the N-oxide form having the formula —$N(O)R_1R_2$.

The anthraquinone group of the molecules of the present invention is found in a number of molecules which have anticancer activity, for example adriamycin and mitoxantrone (Islam et al., 1985, J. Med. Chem., 28: 857). In adriamycin the anthraquinone group is present as part of an anthracycline structure. Typically, drugs containing the anthraquinone group show cross-resistance with adriamycin, i.e. anthraquinone analogues usually show poor activity against adriamycin resistant tumours. Thus it is particularly surprising that even though the molecules of the present invention contain the anthraquinone group they exhibit potent activity against adriamycin resistant tumours.

Furthermore, the molecules of the present invention also show activity against cisplatin resistant tumours. The anticancer drug cisplatin is a metallating agent which, in common with antitumour alkylating agents, function as DNA cross-linking agents. It is also normal for tumours to show cross-resistance against agents which function in this manner, and so alkylating agents will usually show poor activity against cisplatin resistant tumours. It is therefore particularly surprising that, despite containing an alkylating group, the molecules of the present invention also display potent activity against cisplatin resistant tumours.

In formula (1), X may be selected from any one of the group of Cl, Br, I, methanesulfonate, benzenesulfonate, and toluenesulfonate ($SO_3CH_3$, $SO_3C_6H_5$ and $SO_3C_6H_4CH_3$), and in particular may be Cl. The amino group linked to the anthraquinone may be primary, R1 and R2 being H. Alternatively it may be secondary, R1 being H and R2 being a C1–4 lower alkyl. Alternatively it may be tertiary, R1 and R2 being C1–4 lower alkyls. For example, $R_1$ and $R_2$ may be $CH_3$. Alternatively, $R_1$ and/or $R_2$ may be based on an alkyl chain but having additional functionality. For example, $R_1$ and/or $R_2$ may have the formula $CH_2CH_2OH$.

For example, a molecule according to the present invention may be the anthraquinone alkylating agent ZP-281 given by formula (2). It has been found (see below) that this compound is an extremely potent anticancer agent that also shows very potent activity against both adriamycin-resistant tumour cells (e.g. 2780AD cells) and cisplatin-resistant tumour cells (e.g. 2780CP cells).

A key structural feature of compounds of this invention, typified by compound (2), is that they differ from other alkylating anthraquinones in that the alkylating groups are confined to one side-arm only. This is in contrast to compounds of formula (3) and (4) which have alkylating groups in both side-arms. The present inventors have found that the configuration represented in formula (1) where the alkylating functionality resides in only one of the side-arms gives rise to potent cytotoxic agents which evade drug efflux pump mediated resistance, and DNA repair mediated resistance. It is these resistance mechanisms that are commonly associated with anticancer drug treatment failure in the clinic, and the compounds of formula (1), exemplified by compound (2), therefore have utility in the treatment of cancer patients who have relapsed following conventional chemotherapy. The prior art neither discloses nor suggests that anthraquinone alkylating agents should bear alkylating groups on one side-arm only of the anthraquinone.

Due to its drug resistance, a particularly difficult cancer to treat by conventional chemotherapy is ovarian cancer. An important finding with the anthraquinone alkylating agents of the present invention is that they show potent antitumour activity in drug resistant ovarian cancer cell lines such as SKOV-3, CH1cisR, 2780AD, and 2780CP. Thus the molecules of the present invention are particularly valuable for the treatment of ovarian cancer.

Molecules according to the present invention may be for use in the treatment of cancer as an anticancer prodrug. The molecules of the present invention may also be in the form of for example an acid addition salt derived from the reaction of an organic or inorganic acid with the molecule. Such salts may be pharmaceutically acceptable.

Also provided according to the present invention is the use of a molecule according to the present invention in the manufacture of a medicament for the treatment of cancer. Also provided is a method of manufacture of a medicament for the treatment of cancer, characterised in the use of a molecule according to the present invention. Also provided is a method of treatment of cancer, comprising the step of administering to a patient a molecule according to the present invention. Appropriate dosages of the molecules of the present invention may be readily determined using simple dose-response assays.

The invention will be further apparent from the following description, with reference to the several figures of the accompanying drawing, which show, by way of example only, forms of anthraquinone alkylating agents.

EXPERIMENTAL

Figure 1:
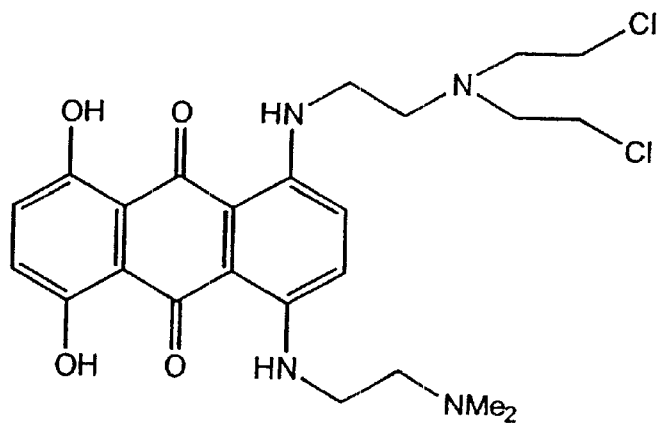
FIG. 1 shows t he compound of formula (2)
Figure 2:
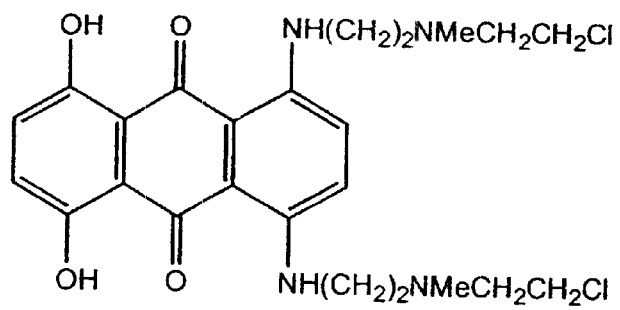
FIG. 2 shows the compound of formula (3)
Figure 3:
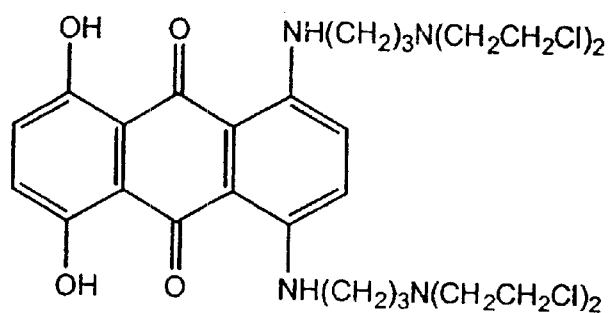
FIG. 3 shows the compound of formula (4).

The compound having formula (2) was synthesised as described below and its anticancer activity against various cell lines, including drug resistant cell lines, tested. Results (below) show compound (2) to have a potent anti-cancer activity even against cisplatin-and adriamycin-resistant cell lines.

Example 1

1-{2-[N,N-bis(2-Chloroethyl)amino]ethyl}amino]-4-[2-(N,N-dimethylamino]ethyl]amino-5,8-dihydroxy-9,10-anthracenedione(DMU Code No. ZP-281): Compound (2)

Synthesis:

Stage 1: Synthesis of N,N-bis(2-Hydroxyethyl)ethylenediamine a) Monoacetylethylenediamine Ethyl acetate (528 g, 6 mol) and ethylenediamine (1550 g, 26 mol) were allowed to stir together at room temperature for several days until the mixture had become homogenous. The unreacted ethyl acetate was removed under reduced pressure and the resulting product collected by high vacuum distillation at 115° C.–130° C. and 5 mm Hg (0.66661 kPa).

b) N-Acetyl-Ni,Ni-bis(2-hydroxyethyl)ethylenediamine

In a liter round bottom flask Monoacetylethylenediamine (150 g, 1.5 mol) was dissolved in methanol (200 ml) and the mixture cooled to 0° C. by keeping the reaction flask on ice and by fixing a liquid nitrogen cold trap to the top of the condenser. Ethylene oxide (194 g, 3 eq) was then added to the flask the mixture stirred at 0° C. for 1 hour and then at room temperature overnight. Following this, ethylene oxide (97 g, 1.5 eq) was again added and the mixture refluxed for 6 hours. The solvent was removed under reduced pressure, and the resulting product collected by high vacuum distillation at 220–230° C., 2 mm Hg (0.266644 kPa).

c) N,N-(2-Hydroxyethyl)ethylenediamine

To N-acetyl-Ni,Ni-bis(2-hydroxyethyl)ethylenediamine (265 g, 1.3 mol) was added 5M HCl (180 ml) and the mixture refluxed for 6 hours. On cooling, the mixture was made basic to pH 8 with 1M NaOH, and the salt removed by precipitation with ethanol. The solvent was removed under reduced pressure and the final product collected by high vacuum distillation at 252–260° C., 5 mm Hg (0.66661 kPa). $^1$H NMR (CDCl$_3$) δ 2.7 (t, 6H, 3CH$_2$N), 2.5 (t, 2CH$_2$NH$_2$), 3.7 (t, 4H, 2CH$_2$OH).

Stage 2: Synthesis of Leuco-4,5,8-tetrahydroxy-anthraquinone a) 1,5-Diamino-4,8-dihydroxyanthraquinone 1,5-Diaminoantraquinone (6 g, 0.025 mol) was dissolved in cooled concentrated H$_2$SO$_4$ (90 g). Maintaining the temperature at 0° C., sodium chlorate(7.2 g, 0.67 mol) was slowly added over a period of 1 hour, after which the mixture was allowed to attain room temperature and left to stir for approximately 3 hours, The reaction mixture was then poured into 1% NaHSO$_3$(1dm$^3$) and the precipitated product washed several times with alternating hot and cold water, filtered and freeze-dried to remove traces of water. The product was obtained as a dark blue powder in 88% yield b) Leuco-1,4,5,8-tetrahydroxyanthraquinone 1,5-Diamino4,8-dihydroxyanthraquinone (6 g, 0.022 mol) and NaOH(12 g, 0.29 mol) were added to distilled water (120 ml) and the mixture warmed to approximately 30° C. Following this, Na$_2$S$_4$ (15 g, 0.88 mol) was added slowly to the sired mixture over a period of 30 min and the reaction refluxed until the blue colour had changed to orange/brown, an indication that the reaction bad gone to completion. After cooling to room temperature the mixture was acidified to pH3 the precipitate removed by filtration, washed with water and dried to give an orange/brown powder, yield 74%.

Stage3: Synthesis of 1-{2-[N,N-bis(2-Chloroethyl)amino]ethyl}amino]-4-[2-(N,N-dimethylamino]ethyl]amino-5,8-dihydroxy-9,10-anthracenedione: Compound (2)

1-{2-[N,N-bis(2-Hydroxyethyl)amino]ethyl}amino]-4-[2-(N,N-dimethylamino]ethyl]amino-5,8-dihydroxy-9,10-anthracenedione (DMU Code No. ZP-275)

Under conditions of a nitrogen atmosphere leuco-1,4,5,8-tetrahydroxyanthraquinone (0.2 g, 0.73 mmol) was added to N,N-bis(2-hydroxyethyl)ethylenediamine (0.67 g, 3.6 mmol) and the mixture allowed to stir for 30 min. To this was then added N,N-dimethylethylenediamine (0.32 g, 3.6 mmol) and the reaction allowed to proceed at 80° C. for 5 hours. After cooling, the mixture was exposed to air on the addition of 15% NaOH(0.2 ml) and the reaction left to stir overnight at room temperature. The crude product was isolated by flash column chromatography and freeze-dried to remove traces of water. Following this, the product was precipitated with methanol-diethylether and dried under vacuum to give a dark-blue powder in 20% yield.

TLC MeOH: CH$_2$Cl$_2$ (50:50), Rf 0.25. $^1$H-NMR(CDCl$_3$/CD3OD) δ 2.4(s, 6H, NCH$_3$), 2.9(t, 6H, 3CH$_2$N), 3.0(t, 2H, CH$_2$N), 3.6(t, 4H, 2CH$_2$NAr), 3.7(t, 4H, 2CH$_2$OH), 7.1(s, 2H, Ar), 7.3(s, 2H, Ar), 10.6(broad t), 2H, NHAr).

1-{2-[N,N-bis(2-chloroethyl)amino]ethyl}amino]-4-[2-(N,N-dimethylamino]ethyl]amino-5,8-dihydroxy-9,10-anthracenedione(DMU Code No. ZP-281): Compound (2)

Under conditions of a nitrogen atmosphere, triphenylphosphine (0.22 g, 0.84 mmol), then carbontetrachloride (0.38 g, 2.5 mmol) were added to a stirred solution of 1- {2-[N,N-bis(2-hydroxyethyl)amino]ethyl}amino]-4-[2-(N,N-dimethylamino]ethyl]amino-5,8-dihydroxy-9,10-anthracenedione (ZP275; 0.1, 0.21 mmol) in a mixture of dichloromethane (4 ml) and acetonitrile (1ml), and the suspension was allowed to stir at room temperature for 48 hours. The crude product was precipitated out by the addition of dry diethyl-ether/hydrogen chloride. Following removal of traces of solvent under vacuum, triphenylphosphine impurities were removed by dissolving the compound in the minimum amount of dichloromethane and methanol, and then precipitating with an ethanol/ethylacetate mixture at 60 ° C. The product was isolated as a dark blue powder in 80% yield.

TLC EtOH:CH$_2$Cl$_2$ (0.5:9.5), Rf=0.75; $^1$H NMR (CDCl$_3$/CD3OD) peaks: δ 3.0(s, 6H, NCH$_3$), 3.4(t, 4H, 2CH$_2$Cl), 3.6(t, 4H, 2CH$_2$NAr), 3.9(t, 8H, 4CH$_2$N), 7.1(s, 2H, Ar), 7.3(s, 2H, Ar), 10.6(broad t), 2H, NHAr); MS MeOH in 3-NBA [M+H]$^+$ m/z=509.

Anticancer Activity Measurements

The cells used for the anticancer activity measurements were the parental ovarian cell line designated as A2780, the doxorubicin-resistant variant designated as 2780AD, and the cisplatin-resistant variant designated as 2780CP (also known as CP70). Drug sensitivity in these cell lines was measured by the standard MTT assay (Carmichael et al., 1987, *Cancer Research*, 47: 936) with a 24 hour drug exposure time. The values obtained are mean values of triplicate measurements.

Results obtained with the compound having formula (2) are summarised in Table 1, together with data for related compounds (3) and (4) for comparison, and show potent antitumour activity in drug resistant ovarian cancer cell lines such as SKOV-3 (Compound 2, IC50=0.49 uM), CH1cisR (0.019 uM), 2780AD (0.016 uM), and 2780CP (0.012 uM).

TABLE 1

Growth Inhibition of Ovarian Cancer Cell Lines (IC$_{50}$/nM)

| Compound | A2780 | 2780AD | 2780CP |
| --- | --- | --- | --- |
| Adriamycin | 5.0 ± 1.1 | 4860 ± 510 | 13.3 ± 0.9 |
| Cisplatin | 340 ± 60 | 3020 ± 220 | 2620 ± 730 |
| Compound (2) | 4.0 ± 0.6 | 16.0 ± 1.7 | 11.8 ± 1.4 |
| Compound (3) | 0.9 ± 0.3 | 573 ± 133 | 14.3 ± 1.0 |
| Compound (4) | 3.0 ± 0.6 | 246 ± 12 | 50.2 ± 3.9 |

Key:
A2780 is the parental ovarian cancer cell line.
2780AD is an adriamycin (doxorubicin) resistant ovarian cancer cell line variant.
2780CP is a cisplatin resistant ovarian cancer cell line variant.

What is claimed is:

1. A molecule of formula (1);

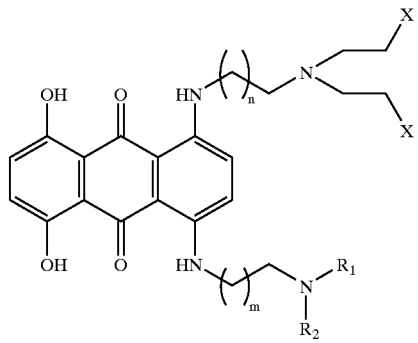

wherein:
X is a halogen, or a substituted sulfonate group;
m=1–5;
n=1–5;
$R_1$, $R_2$=H, $C_1$–$C_4$ lower alkyl or $C_1$–$C_4$ lower alkyl chain having functionality; and
the amino group —$NR_1R_2$ linked to the anthraquinone is primary, secondary or tertiary or is a tertiary group in the N-oxide form having the formula —$N(O)R_1R_2$.

2. A molecule according to claim 1, X being selected from the group consisting of: Cl, Br, I, $SO_3CH_3$, $SO_3C_6H_5$ and $SO_3C_6H_4CH_3$.

3. A molecule according to claim 2, X being Cl.

4. A molecule according to claim 1, the amino group linked to the anthraquinone being primary, R1 and R2 being H.

5. A molecule according to claim 1, the amino group linked to the anthraquinone being secondary, R1 being H and R2 being $C_1$–$C_4$ lower alkyl.

6. A molecule according to claim 1, the amino group linked to the anthraquinone being tertiary, R1 and R2 being $C_1$–$C_4$ lower alkyls.

7. A molecule according to claim 6, $R_1$ and $R_2$ being $CH_3$.

8. A molecule according to claim 1, $R_1$ or $R_2$ having the formula $CH_2CH_2OH$.

9. A molecule according to claim 1, wherein m=1 and n=1.

10. A molecule according to claim 9, having the formula (2).

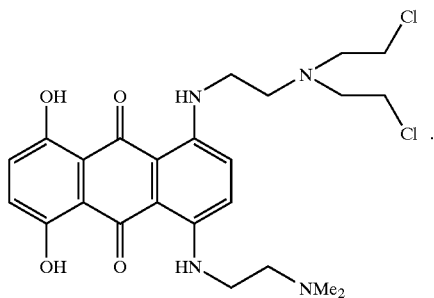

11. A molecule according to claim 1, being in the form of an acid addition salt derived from the reaction of an organic or inorganic acid with the molecule.

12. A method of manufacture of a medicament for the treatment of cancer, comprising a step of using the molecule of claim 1 in the method of manufacture.

13. A method of treatment of cancer, comprising the step of administering to a patient in need thereof a molecule according to claim 1.

14. The method of treatment of cancer according to claim 13, wherein the step of administering to said patient said molecule further comprises administering to said patient having drug resistant tumors.

15. The method of treatment of cancer according to claim 13, wherein the step of administering to said patient said molecule, further comprises administering to said patient having ovarian cancer.

* * * * *